US009102579B2

(12) United States Patent
Light et al.

(10) Patent No.: US 9,102,579 B2
(45) Date of Patent: Aug. 11, 2015

(54) METHOD FOR PRODUCING FLUORINATED ORGANIC COMPOUNDS

(75) Inventors: Barbara A. Light, Niagara Falls, NY (US); Steven D. Phillips, Buffalo, NY (US); Kim M. Fleming, Hamburg, NY (US); Susan A. Ferguson, Orchard Park, NY (US); Jing Ji Ma, West Seneca, NY (US); Cheryl L. Bortz, N. Tonawanda, NY (US); Michael Van Der Puy, Amherst, NY (US); Daniel C. Merkel, West Seneca, NY (US); Hsueh S. Tung, Getzville, NY (US); Sudip Mukhopadhyay, Williamsville, NY (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 1754 days.

(21) Appl. No.: 11/619,589

(22) Filed: Jan. 3, 2007

(65) Prior Publication Data

US 2007/0197841 A1   Aug. 23, 2007

Related U.S. Application Data

(63) Continuation-in-part of application No. 11/118,504, filed on Apr. 29, 2005, now Pat. No. 7,371,904, and a continuation-in-part of application No. 11/118,503, filed on Apr. 29, 2005, now Pat. No. 7,345,209, and a continuation-in-part of application No. 11/118,530, filed on Apr. 29, 2005, now Pat. No. 7,189,884.

(60) Provisional application No. 60/755,486, filed on Jan. 3, 2006, provisional application No. 60/567,426, filed on Apr. 29, 2004, provisional application No. 60/567,429, filed on Apr. 29, 2004, provisional application No. 60/567,427, filed on Apr. 29, 2004, provisional application No. 60/567,425, filed on Apr. 29, 2004, provisional application No. 60/567,428, filed on Apr. 29, 2004.

(51) Int. Cl.

| C07C 17/00 | (2006.01) |
|---|---|
| C07C 19/08 | (2006.01) |
| C07C 21/18 | (2006.01) |
| C07C 23/00 | (2006.01) |
| C07C 25/13 | (2006.01) |
| C07C 17/21 | (2006.01) |
| C07C 17/087 | (2006.01) |
| C07C 17/10 | (2006.01) |
| C07C 17/20 | (2006.01) |
| C07C 17/25 | (2006.01) |

(52) U.S. Cl.
CPC .............. *C07C 17/21* (2013.01); *C07C 17/087* (2013.01); *C07C 17/10* (2013.01); *C07C 17/206* (2013.01); *C07C 17/25* (2013.01); *C07C 19/08* (2013.01)

(58) Field of Classification Search
None
See application file for complete search history.

(56) References Cited

U.S. PATENT DOCUMENTS

| 2,931,840 | A | 4/1960 | Marquis ..................... 260/653.3 |
|---|---|---|---|
| 2,996,555 | A | 8/1961 | Rausch et al. |
| 3,472,826 | A | 10/1969 | Potts et al. |
| 3,659,023 | A | 4/1972 | Regan |
| 4,086,407 | A | 4/1978 | Fozzard ........................ 526/75 |
| 4,650,914 | A | 3/1987 | Woodard et al. |
| 4,798,818 | A | 1/1989 | Baizer et al. |
| 4,900,874 | A | 2/1990 | Ihara et al. |
| 5,532,419 | A * | 7/1996 | Van Der Puy et al. ........ 570/167 |
| 5,545,777 | A | 8/1996 | Morikawa et al. |
| 5,574,192 | A | 11/1996 | Van Der Puy et al. |
| 5,679,875 | A | 10/1997 | Aoyama et al. |
| 5,986,151 | A | 11/1999 | Van Der Puy et al. |
| 6,111,150 | A | 8/2000 | Sakyu et al. |
| 6,124,510 | A * | 9/2000 | Elsheikh et al. .............. 570/156 |
| 6,369,284 | B1 | 4/2002 | Nappa et al. |
| 6,548,719 | B1 | 4/2003 | Nair et al. |
| 6,809,226 | B1 | 10/2004 | Pennetreau et al. |
| 6,958,424 | B1 | 10/2005 | Nair et al. |
| 7,189,884 | B2 * | 3/2007 | Mukhopadhyay et al. ... 570/160 |
| 7,345,209 | B2 * | 3/2008 | Mukhopadhyay et al. ... 570/157 |
| 7,371,904 | B2 * | 5/2008 | Ma et al. ....................... 570/136 |
| 7,659,434 | B2 * | 2/2010 | Mukhopadhyay et al. ... 570/136 |
| 7,674,939 | B2 * | 3/2010 | Mukhopadhyay et al. ... 570/156 |
| 7,700,815 | B2 * | 4/2010 | Tung et al. .................... 570/153 |
| 2003/0060670 | A1 | 3/2003 | Nair et al. ..................... 570/155 |

(Continued)

FOREIGN PATENT DOCUMENTS

| EP | 522639 | 1/1993 |
|---|---|---|
| EP | 0522639 | 1/1993 |

(Continued)

OTHER PUBLICATIONS

JP2000169404 Derwent Abstract (Jun. 2000) p. 1-2.*
Montanari V: "A Novel Synthesis of Perhalogenated Alkenes" Journal of Organic Chemistry, vol. 57, No. 3, 1992, pp. 5018-5019 XP002426455.
McDoniel JB, et al Threshold Energy and Unimolecular Rate Constant for . . . CF3CF2CH3, J Phys Chem, vol. 101, No. 7, 1997, pp. 1334-1337 XP-002426456.
EP Exam Report issued in EP07716234.5 dated Aug. 22, 2013.

(Continued)

*Primary Examiner* — Clinton Brooks
(74) *Attorney, Agent, or Firm* — Bruce Bradford

(57) ABSTRACT

Disclosed is a process for producing fluorinated organic compounds, including hydrofluoropropenes, which preferably comprises converting at least one compound of Formula (I):

$$C(X)_3CF_2C(X)_3 \quad (I)$$

to at least one compound of Formula (II)

$$CF_3CF=CHZ \quad (II)$$

where each X and Z is independently H, F, Cl, I or Br, said process preferably not including any substantial amount of oxygen-containing catalyst in certain embodiments. Preferably Z is H.

19 Claims, No Drawings

(56) References Cited

U.S. PATENT DOCUMENTS

| | | |
|---|---|---|
| 2005/0020862 A1 | 1/2005 | Tung et al. |
| 2005/0080302 A1 | 4/2005 | Baker et al. |
| 2005/0090698 A1 | 4/2005 | Merkel et al. |
| 2005/0171391 A1 | 8/2005 | Janssens et al. |

FOREIGN PATENT DOCUMENTS

| | | |
|---|---|---|
| JP | 2-17138 A | 1/1990 |
| JP | 2-204437 A | 8/1990 |
| JP | 8-169850 A | 7/1996 |
| JP | 11-140002 A | 5/1999 |
| JP | 11140002 | 5/1999 |
| JP | 2000169404 | 6/2000 |
| WO | WO 9504021 | 2/1995 |
| WO | WO/96/01797 A | 1/1996 |
| WO | WO 98/21171 | 5/1998 |
| WO | WO 01/07384 | 2/2001 |
| WO | 2005012212 A2 | 2/2005 |
| WO | WO2005/042451 A | 5/2005 |
| WO | 2007053178 A1 | 5/2007 |
| WO | 2007053736 A2 | 5/2007 |
| WO | 2007056128 A1 | 5/2007 |
| WO | 2007086972 A2 | 8/2007 |

OTHER PUBLICATIONS

Corresponding—Office Action in Japanese Application No. 2008-548885, dated Nov. 26, 2013—enclosing record of prior art search result.

McDoniel JB, et al, Threschold Energy and Unimolecular Rate Constant for Elimination of HF from Chemically Activated $CF_3CF_2CH_3$: Effect of the $CF_3$ Substituent on the alpha-Carbon, J. Phys. Chem. A, 1997, pp. 1334-1337, vol. 101, XP-002429690.

Okrkin VL, et al., "Rate Constants for the Reactions of OH with HFC-245cb ($CH_3CF_2CF_3$) and Some Fluoroalkenes ($CH_2CHCF_3$, $CH_2CFCF_3$, $CF_2CFCF_3$, and $CF_2CF_2$)", J. Phys. Chem. A, 1997, pp. 9118-9124, vol. 101, XP-002429691.

U.S. Appl. No. 10/694,273, filed Oct. 27, 2003, Singh et al.

Zhuranl Organicheskoi Khimii, 28(4), 672-80, (1982).

Free-radical additions to unsaturated systems, Journal of Chemical Society, Section C: Organic, (3), 414-21, p. 415, 1970.

* cited by examiner

METHOD FOR PRODUCING FLUORINATED ORGANIC COMPOUNDS

CROSS-REFERENCES TO RELATED APPLICATIONS

This application is related to and claims the priority benefit of U.S. provisional application No. 60/755,486, filed Jan. 3, 2006.

This application is a Continuation-in-Part of U.S. patent application Ser. No. 11/118,503, (pending) filed on Apr. 29, 2005, which in turn claims the priority benefit of U.S. Provisional Patent Application Nos. 60/567,427 and 60/567,425 filed Apr. 16, 2004.

This application is also a Continuation-in-Part of U.S. patent application Ser. No. 11/118,504, (pending) filed on Apr. 29, 2005, which in turn claims the priority benefit of U.S. Provisional Patent Application Nos. 60/567,426 and 60/567,429 filed Apr. 16, 2004.

This application is also a Continuation-in-Part of U.S. patent application Ser. No. 11/118,530, (pending) filed on Apr. 29, 2005, which in turn claims the priority benefit of U.S. Provisional Patent Application No. 60/567,428.

The disclosures of each of the above-mentioned applications are incorporated herein by reference. Also incorporated herein by reference are the following U.S. Application 60/733,378; 60/733,444; 60/733,383; 60/733,355 and 60/733,379 each of which was filed on Nov. 3, 2005.

BACKGROUND OF INVENTION (1) Field of Invention

This invention relates to novel methods for preparing fluorinated organic compounds.

(2) Description of Related Art

Hydrofluorocarbons (HFC's), in particular hydrofluoroalkenes such tetrafluoropropenes (including 2,3,3,3-tetrafluoro-1-propene (HFO-1234yf) and 1,3,3,3-tetrafluoro-1-propene (HFO-1234ze)) have been disclosed to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFCs do not contain chlorine and thus pose no threat to the ozone layer.

Several methods of preparing hydrofluoroalkenes are known. For example, U.S. Pat. No. 4,900,874 (Ihara et al) describes a method of making fluorine containing olefins by contacting hydrogen gas with fluorinated alcohols. Although this appears to be a relatively high-yield process, for commercial scale production the handling of hydrogen gas at high temperature raises difficult safety related questions. Also, the cost of producing hydrogen gas, such as building an on-site hydrogen plant, can be in many situations prohibitive.

U.S. Pat. No. 2,931,840 (Marquis) describes a method of making fluorine containing olefins by pyrolysis of methyl chloride and tetrafluoroethylene or chlorodifluoromethane. This process is a relatively low yield process and a very large percentage of the organic starting material is converted in this process to unwanted and/or unimportant byproducts.

U.S. Pat. No. 2,996,555 (Rausch) describes a method for the vapor phase manufacture of fluorine containing olefins by a single step process in which an oxygen-containing metal catalyst, such as chromium oxyfluoride, is used to convert a compound of formula CX3CF2CH3 to 2,3,3,3-tetrafluoropropenen. This examples in this patent describe a process which produces a relatively low yield, that is, 60%.

The preparation of HFO-1234yf from trifluoroacetylacetone and sulfur tetrafluoride has been described. See Banks, et al., *Journal of Fluorine Chemistry*, Vol. 82, Iss. 2, p. 171-174 (1997). Also, U.S. Pat. No. 5,162,594 (Krespan) discloses a process wherein tetrafluoroethylene is reacted with another fluorinated ethylene in the liquid phase to produce a polyfluoroolefin product.

SUMMARY

Applicants have discovered a method for producing fluorinated organic compounds, including hydrofluoropropenes, which preferably comprises converting at least one compound of Formula (I):

$$C(X)_3CF_2C(X)_3 \tag{I}$$

to at least one compound of Formula (II)

$$CF_3CF=CHZ \tag{II}$$

where each X and Z is independently H, F, Cl, I or Br, said process preferably not including any substantial amount of oxygen-containing catalyst in certain embodiments. Preferably Z is H. As used herein and throughout, unless specifically indicated otherwise, the term "converting" includes directly converting (for example, in a single reaction or under essentially one set of reaction conditions, and example of which is described hereinafter) and indirectly converting (for example, through two or more reactions or using more than a single set of reaction conditions).

In certain preferred embodiments of the invention, the compound of Formula (I) comprises a compound wherein each X on one terminal carbon is H, wherein each X on the other terminal carbon is independently selected from F, Cl, I or Br. Such preferred embodiments include converting at least one C3 alkane of Formula (IA):

$$C(X)_3CF_2CH_3 \tag{IA}$$

to at least one compound of formula (II)

$$CF_3CF=CHZ \tag{II}$$

where each X is independently F, Cl, Br or I, said process preferably not including any substantial amount of oxygen-containing catalyst in certain embodiments. Preferably Z in such embodiments is H.

Preferably the compounds of Formula (I) contain at least four halogen substituents and even more preferably at least five halogen substituents. In certainly highly preferred embodiments, the conversion step of the present invention comprises converting a compound of Formula (IA) wherein each X is F. Preferably the compound of Formula (IA) is a penta-halogenated. Even more preferably the penta-halogenated propane of Formula (IA) comprises a trichlorinated, difluorinated propane, penta-fluorinated propane, and combinations of these.

Preferred compounds of Formula (IA) include 1,1,1-trichloro-2,2-difluoropropane (HCFC-242bb), and 1,1,1,2,2-pentafluoropropane (HFC-245cb).

In certain preferred embodiments, the step of converting a compound of Formula (I) to at least one compound of Formula (II) comprises directly converting a compound of Formula (I). In other embodiments, the step of converting a compound of Formula (I) to at least one compound of Formula (II) comprises indirectly converting a compound of Formula (I).

An example of such indirect conversion embodiments includes converting a first compound of Formula (I), for example HCFC-242bb, to a second compound of Formula (I), for example, HFC-245cb, and then converting the second Formula (I) compound to a Formula (II) compound. In certain more specific indirect conversion embodiments, the step of converting a compound of Formula (I) comprises providing at least one trichlorodifluorpropane in accordance with Formula (IA), preferably $CCl_3CF_2CH_3$ (HCFC-242bb) and reacting same under conditions effective to produce at least one pentafluorpropane in accordance with Formula (IA), preferably $CF_3CF_2CH_3$ (HFC-245cb), which in turn is preferably exposed to reaction conditions effective to produce at least one compound in accordance with Formula (II), preferably HFO-1234yf. In preferred embodiments said exposing step comprises conducting one or more of said reactions in a gas and/or liquid phase in the presence of a catalyst, preferably a metal-based catalyst. Examples of such preferred conversion steps are disclosed more fully hereinafter. Of course, it is contemplated that in the broad scope of the invention that any of the Formula (I) compounds may be converted, directly or indirectly, to a compound of Formula (II) in view of the teachings contained herein.

In certain preferred embodiments the converting step comprises exposing the compound of Formula (I), and preferably Formula (1A) to one or more sets of reaction conditions effective to produce at least one compound in accordance with Formula (II).

The preferred conversion step of the present invention is preferably carried out under conditions, including the use of one or more reactions, effective to provide a Formula (I) conversion of at least about 50%, more preferably at least about 75%, and even more preferably at least about 90%. In certain preferred embodiments the conversion is at least about 95%, and more preferably at least about 97%. Further in certain preferred embodiments, the step of converting the compound of Formula (I) to produce a compound of Formula (II) is conducted under conditions effective to provide a formula (II) selectivity of at least about 45%, more preferably at least about 55%, and more preferably at least about 75%. In certain preferred embodiments a selectivity of about 95% or greater may be achieved.

In other aspects of the present invention, a method is provided for producing the compound of Formula (I) by converting at least one compound of Formula (III):

$$C(X)_2—CClC(X)_3 \qquad (III)$$

to at least one compound of Formula (I), as described above, where each X is independently H, F, Cl, I or Br, provided at least one X is Cl, I or Br. In preferred embodiments, at least one X on the unsaturated carbon is Cl, I or Br, and even more preferably Cl. The details of exemplary conversion steps in accordance with this aspect of the invention are provided in the examples.

DETAILED DESCRIPTION OF PREFERRED EMBODIMENTS

One beneficial aspect of the present invention is that it enables the production of desirable fluroolefins, preferably C3 fluoroolefins, using relatively high conversion and high selectivity reactions. Furthermore, the present methods in certain preferred embodiments permit the production of the desirable fluoroolefins, either directly or indirectly, from relatively attractive starting materials.

Preferably the Formula (I) compound is exposed to reaction conditions effective to produce a reaction product containing one or more of the desired fluorolefins, preferably one or more compounds of Formula (II). Although it is contemplated that the exposure step in certain embodiments may effectively be carried out in a single reaction stage and/or under a single set of reaction conditions, as mentioned above, it is preferred in many embodiments that the conversion step comprise a series of reaction stages or conditions. In one preferred aspect of the present invention, the conversion step comprises: (a) reacting a first chlorinated compound of Formula (IA), in a gas and/or liquid phase reaction in the presence of at least a first catalyst to produce at least one compound of Formula (IA), preferably a compound of Formula (IA) which is penta-fluorinated, and even more preferably contains no other halogen substituents, such as HFC-245; (b) reacting the Formula (IA) compound, preferably the penta-fluorinated Formula (IA) compound, preferably in a gas phase and in the presence or absence of catalyst, which if present maybe the same or different than the first catalyst to produce at least one compound of Formula (II) and even more preferably HFO-1234yf. In certain embodiments, the catalyst does not include substantial amounts of oxygen containing catalyst. Each of the preferred reaction steps is described in detail below, with the headings being used for convenience but not necessarily by way of limitation.

I. Fluorination of the Multi-Halogenated Formula I(a)

One preferred reaction step in accordance may be described by those reactions in which the compound of Formula (IA) contains fluorine and at least one other halogen, and this compound is fluorinated to produce a compound of Formula (IA) which contains at least four, and preferably five, fluorine substituents, and even more preferably no other halogen substituents. In certain of such preferred embodiments, especially embodiments in which such compound comprises HCFC-242bb, the present converting step comprises first reacting said compound(s) by fluorinating said compound(s), preferably with HF in a gas and/or liquid phase, to produce an HFC, preferably an HFC that is at least tetrafluorinated, such as HFC-245. Preferably this reaction, whether in the gas phase, the liquid phase, or both is at least partially catalyzed. In certain preferred embodiments, the compound of Formula (IA), such as HCFC-242bb is contacted with liquid HF in the presence of a catalyst including but not limited to $SbCl_5$, $SbF_5$, $SbF_3$, $TiCl_4$, $SnCl_4$, $FeCl_3$, $AlCl_3$, $AlF_3$, and combinations of two or more of these, to synthesize a compound of Formula (IA) having an increased number of fluorine substituents, and preferably only fluorine substituents, such as $CF_3CF_2CH_3$. $SbCl_5$ is found to be highly preferred in many desirable embodiments. In other preferred embodiments, this conversion step is carried out in a catalytic, continuous, gas-phase reaction mode using $SbCl_5/C$ as the solid catalyst. The preferred fluorination of the compound of Formula (IA) is preferably carried out under conditions effective to provide a Formula (IA) conversion of at least about 50%, more preferably at least about 75%, and even more preferably at least about 90%. In certain preferred embodiments the conversion is at least about 95%, and more preferably at least about 97%. Further in certain preferred embodiments, the conversion of the compound of Formula (IA) comprises reacting such compound under conditions effective to produce at least one penta-fluorinated compound (preferably HFC-245) at a yield of at least about 70%, more preferably at least about 75%, and even more preferably at least about 80%.

In general, it is possible that the fluorination reaction step can be carried out in the liquid phase or in the gas phase, or in a combination of gas and liquid phases, and it is contemplated that the reaction can be carried out batch wise, continuous, or a combination of these.

In preferred gas phase fluorination of Formula (I) compounds, the reaction is at least partially a catalyzed reaction, and is preferably carried out on a continuous basis by introducing a stream containing the compound of Formula (I) into one or more reaction vessels, such as a tubular reactor. In certain preferred embodiments, the stream containing the compound of Formula (I), and preferably Formula (IA), is preheated to a temperature of from about 150° C. to about 400° C., preferably about 300° C., and introduced into a reaction vessel (preferably a tube reactor), which is maintained at the desired temperature, preferably from about 40° C. to about 200° C., more preferably from about 50° C. to about 150° C., where it is preferably contacted with catalyst and fluorinating agent, such as HF.

Preferably the vessel is comprised of materials which are resistant to corrosion as Hastelloy, Inconel, Monel and/or fluoropolymers linings.

Preferably the vessel contains catalyst, for example a fixed or fluid catalyst bed, packed with a suitable fluorination catalyst, with suitable means to ensure that the reaction mixture is maintained with the desired reaction temperature range.

Thus, it is contemplated that the fluorination reaction step may be performed using a wide variety of process parameters and process conditions in view of the overall teachings contained herein. However, it is preferred in certain embodiments that this reaction step comprise a gas phase reaction, preferably in the presence of catalyst, and even more preferably a Sb-based and/or and Fe-based catalyst (such as $FeCl_3$ on carbon (designated herein as $FeCl_3/C$ for convenience), and combinations of these.

In general it is also contemplated that a wide variety of reaction pressures may be used for the fluorination reaction, depending again on relevant factors such as the specific catalyst being used and the most desired reaction product. The reaction pressure can be, for example, superatmospheric, atmospheric or under vacuum, and in certain preferred embodiments is from about 1 to about 200 psia, and even more preferably from about 1 to about 120 psia.

In certain embodiments, an inert diluent gas, such as nitrogen, may be used in combination with the other reactor feed(s).

It is contemplated that the amount of catalyst use will vary depending on the particular parameters present in each embodiment.

II. Conversion to Formula (II)

One preferred reaction step in accordance may be described by those reactions in which the compound of Formula (I), preferably Formula (IA) is converted to a compound of Formula (II). In certain preferred embodiments, the stream containing the compound of formula (I), and preferably (IA) is preheated to a temperature of from about 150° C. to about 400° C., preferably about 350° C., and introduced into a reaction vessel, which is maintained at the desired temperature, preferably from about 300° C. to about 700° C., more preferably from about 450° C. to about 650° C.

Preferably the vessel is comprised of materials which are resistant to corrosion as Hastelloy, Inconel, Monel and/or fluoropolymers linings. Preferably the vessel contains catalyst, for example a fixed or fluid catalyst bed, packed with a suitable catalyst, with suitable means to heat the reaction mixture to the desired reaction temperature.

Thus, it is contemplated that this reaction step may be preformed using a wide variety of process parameters and process conditions in view of the overall teachings contained herein. However, it is preferred in certain embodiments that this reaction step comprise a gas phase reaction, preferably in the presence of catalyst, and even more preferably a carbon- and/or metal-based catalyst, preferably activated carbon, a nickel-based catalyst (such as Ni-mesh) and combinations of these. Other catalysts and catalyst supports may be used, including palladium on carbon, palladium-based catalyst (including palladium on aluminum oxides), and it is expected that many other catalysts may be used depending on the requirements of particular embodiments in view of the teachings contained herein. Of course, two or more any of these catalysts, or other catalysts not named here, may be used in combination.

While it is contemplated that a wide variety of reaction temperatures may be used, depending on relevant factors such as the catalyst being used and the most desired reaction product, it is generally preferred that the reaction temperature for the step is from about 200° C. to about 800° C., more preferably from about 400° C. to about 800° C. In certain preferred embodiments, the reaction temperature is from about 300° C. to about 600° C., and even more preferably in certain embodiments from about 500° C. to about 600° C.

In general it is also contemplated that a wide variety of reaction pressures may be used, depending again on relevant factors such as the specific catalyst being used and the most desired reaction product. The reaction pressure can be, for example, superatmospheric, atmospheric or under vacuum and in certain preferred embodiments is from about 1 to about 200 psia, and in certain embodiment from about 1 to about 120 psia.

In certain embodiments, an inert diluent gas, such as nitrogen, may be used in combination with the other reactor feed(s). It is contemplated that the amount of catalyst use will vary depending on the particular parameters present in each embodiment.

Preferably in such embodiments as described in this section, the conversion of the formula (I) compound is at least about 30%, more preferably at least about 50%, and even more preferably at least about 60%. Preferably in such embodiments, the selectivity to compound of Formula (II), preferably HFO-1234yf, is at least about 70%, more preferably at least about 80% and more preferably at least about 90%.

EXAMPLES

Additional features of the present invention are provided in the following examples, which should not be construed as limiting the claims in any way.

Examples 1A

Liquid-Phase Catalytic Fluorination of $CCl_3CF_2CH_3$ (242bb) with HF to $CF_3CF_2CH_3$ (R245cb)

Example 1A

About 327 grams HF, about 50 grams $CCl_3CF_2CH_3$ (242bb), and about 75 grams $SbCl_5$ were charged into a 1-L autoclave. The reaction mixture was stirred at 120° C. for about 6 hours under about 760 psig of pressure. After the stipulated reaction time, the reactor was cooled up to about 0° C., and about 300 ml water was then added slowly into the autoclave over a period of about 45 minutes. After complete addition of water under stirring, the reactor was heated to about 70° C. and then the overhead gases were transferred to another collecting cylinder. The yield of $CF_3CF_2CH_3$ was about 82% at a 242bb conversion level of about 100%. The other major by-products were traces of $CF_3CFClCH_3$ and tarry material.

Example 1B

About 327 grams of HF, about 50 grams of $CCl_3CF_2CH_3$ (242bb), and about 75 grams of $SbCl_5$ were charged into a 1-L autoclave. The reaction mixture was stirred at about 100° C. for about 6 hours under about 620 psig of pressure. After the reaction, the reactor was cooled to about 0° C., and about 300 ml water was then added slowly into the autoclave over a period of about 45 minutes. After complete addition of water under stirring, the reactor temperature was raised to 70° C. and then the overhead gases were transferred to another collecting cylinder. The yield of $CF_3CF_2CH_3$ was about 78% at a 242bb conversion level of about 86%. The other major by-products were traces of $CF_3CFClCH_3$ and other clorofluoropropanes.

Example 1C

About 327 grams HF, about 50 grams 1233xf, and about 75 grams $SbCl_5$ were charged into a 1-L autoclave. The reaction mixture was stirred at about 80° C. for about 6 hours under about 460 psig of pressure. After the reaction, the reactor was cooled to 0° C. and 300 ml water was then added slowly into the autoclave over a period of about 45 minutes. After complete addition of water under stirring, the reactor was cooled to room temperature and then the overhead gases were transferred to another collecting cylinder. The yield of $CF_3CF_2CH_3$ was about 67%. The only other major by-products includes products resulted from incomplete fluorination and trace of $CF_3CFClCH_3$.

Example 2

Gas-Phase Catalytic Fluorination of $CCl_3CF_2CH_3$ (242bb) with HF to $CF_3CF_2CH_3$ (R245cb)

A 22-inch (½-inch diameter) Monel pipe gas phase reactor was charged with 120 cc of 50 wt % $SbCl_5/C$ as the catalyst. The reactor was mounted inside a heater with three zones (top, middle and bottom). The reactor temperature was read by custom made 5-point thermocouples kept at the middle inside of the reactor. The inlet of the reactor was connected to a pre-heater, which was kept at about 300° C. by electrical heating. The liquid-HF was fed from a cylinder into the pre-heater through a needle valve, liquid mass-flow meter, and a research control valve at a substantially constant flow of from about 1 to about 1000 grams per hour (g/h). The HF cylinder was kept at a constant pressure of 45 psig by applying anhydrous $N_2$ gas pressure into the cylinder head space. A feed consisting of organic reactant (242bb) was fed at a rate ranging from about 10 to about 120 g/h as a gas from a cylinder kept at about 145° C. through a regulator, needle valve, and a gas mass-flow-meter. The organic feed stream was also fed periodically as liquid at about 105° C. from a cylinder into the pre-heater through a needle valve, liquid mass-flow meter, and a research control valve at a substantially constant flow rate ranging from about 10 to about 150 g/h. The organic line from the cylinder to the pre-heater was kept at about 265° C. by wrapping with constant temperature heat trace and electrical heating. All feed cylinders were mounted on scales to monitor their weight by difference. The reactions were run at a substantially constant reactor pressure of from about 0 to about 100 psig by controlling the flow of reactor exit gases by another research control valve. The exit gases coming out of the reactor were analyzed by on-line GC and GC/MS connected through a hotbox valve arrangements to prevent condensation. The reactor temperature was kept at from about 60° C. to about 120° C. The $SbCl_5/C$ catalyst was pretreated with about 50 g/h HF at about the reaction temperature for about 8 hours under about 50 psig pressures. After HF pretreatment, the catalyst was further treated with about 20 sccm of $Cl_2$ and about 50 g/h of HF for an additional 4 hours. The pretreated catalyst was then contacted with organic in the presence of about 50 g/h HF. The conversion of 242bb was in the range of from about 60 to about 70% and the selectivity to 245cb was about 85% when the reaction was performed using 50 wt % $SbCl_5/C$ as the catalyst at about 120° C. under about 30 psig pressure in the presence of about 50 g/h HF and about 20 g/h of 242bb. The product was collected by flowing the reactor exit gases through a solution of from about 20 wt % to about 60 wt % aqueous KOH scrubber solution and then trapping the exit gases from the scrubber into a cylinder kept in dry ice or liquid $N_2$. The products were then isolated by distillation. The following catalysts were tested and found to have the selecetivity to HFC-245 as indicated in parenthesis: 30 wt % $SbCl_5/C$ (Sel. 81%); from about 3 to about 6 wt % $FeCl_3/C$ (Sel. 52%); $SbF_5/C$ (Sel. 87%); 20 wt % $SnCl_4/C$ (Sel. 32%); 23 wt % $TiCl_4/C$ (Sel. 27%). The catalyst temperatures o used ranged from about 60° C. to about 120° C. $SbCl_5/C$ is believed to be a preferred catalyst for this gas-phase transformation.

Example 3

Catalytic Conversion of $CF_3CF_2CH_3$ to $CF_3CF=CH_2$

A 22-inch (½-inch diameter) Monel tube reactor was charged with about 120 cc of a catalyst. The reactor was mounted inside a heater with three zones (top, middle and bottom). The reactor temperature was read by custom made 5-point thermocouples kept at the middle inside of the reactor. The inlet of the reactor was connected to a pre-heater, which was kept at about 300° C. by electrical heating. HFC-245cb was fed from a cylinder kept at about 65° C. through a regulator, needle valve, and a gas mass-flow-meter. The line to the pre-heater was heat traced and kept at a substantially constant temperature of from about 65° C. to about 70° C. by electrical heating to avoid condensation. The feed cylinder was mounted on scales to monitor their weight by difference. The reactions were run at a substantially constant reactor pressure in the range of from about 0 to about 100 psig by controlling the flow of reactor exit gases by another research control valve. The gas mixture exiting the reactor was analyzed by on-line GC and GC/MS connected through a hotbox valve arrangements to prevent condensation. The conversion of 245cb was in the range of from about 30% to about 70% and the selectivity to HFO-1234yf was in the range of from about 90% to about 100% depending on the reaction conditions. The products were collected by flowing the reactor exit gases through a 20-60-wt % of aqueous KOH scrubber solution and then trapping the exit gases from the scrubber into a cylinder kept in dry ice or liquid $N_2$. The products were then substantial isolated by distillation. Results are tabulated in Table 1.

TABLE 1

Transformation of $CF_3CF_2CH_3$ to 1234yf

| # | Cat | T, ° C. | $H_2$, sccm | $CF_3CF_2CH_3$ (245cb) sccm | Conversion of 245cb | 1234yf (Sel. %) |
|---|-----|---------|-------------|------------------------------|---------------------|------------------|
| 1 | A | 575 | 0 | 65 | 79 | 63 |
| 2 | B | 575 | 0 | 68 | 82 | 57 |
| 3 | C | 575 | 0 | 73 | 73 | 61 |
| 4 | D | 575 | 0 | 68 | 84 | 59 |
| 5 | D | 575 | 20 | 68 | 89 | 73 |
| 6 | E | 550 | 0 | 69 | 92 | 53 |

TABLE 1-continued

Transformation of CF$_3$CF$_2$CH$_3$ to 1234yf

| # | Cat | T, °C. | H$_2$, sccm | CF$_3$CF$_2$CH$_3$ (245cb) sccm | Conversion of 245cb | 1234yf (Sel. %) |
|---|-----|--------|-------------|-------------------------------|---------------------|-----------------|
| 7 | F   | 550    | 0           | 67                            | 93                  | 33              |
| 8 | G   | 550    | 0           | 69                            | 73                  | 46              |

Reaction conditions: Pressure about 2.5 to about 5.3 psig; Catalyst, 100 cc":
A is NORIT RFC 3; B is Shiro-Saga activated carbon; C is Aldrich activated carbon; D is Calgon activated carbon; E is 0.5 wt % Pd/C; F is 0.5 wt % Pt/C; G is Ni-mesh; Organic cylinder temperature about 65° C.; CF$_3$CF$_2$CH$_3$ (245cb) line to the preheater about 50° C.; Preheater, 350° C.; N$_2$-0 sccm.

Example 4A-4C

Preparation of CH3CF2CH2Cl from 2,3-dichloropropene Using HF/SbCl$_5$

Example 4A

A 2-gallon autoclave was charged with about 900 grams (8.1 mol) of 2,3-dichloropropene, about 405 grams (20.3 mol) of HF, and about 10 grams (0.033 mol) of SbCl$_5$. The contents were heated with stirring to about 100° C. for about 19 hours. The maximum pressure was about 285 psig. (approx. 2000 kPa). The contents were vented while hot into a fluoropolymer container containing ice, which was connected in sequence to a dry ice trap. The organic layer was separated and washed to remove residual acid, giving about 811.9 grams of crude product, which by GC analysis was comprised of about 41% CH$_3$CF$_2$CH$_2$Cl, about 34.5% CH$_3$CFClCH$_2$Cl, 21% CH$_3$CCl$_2$CH$_2$Cl, and about 1.8% starting material. The conversion was about 97%, while the combined yield of halopropanes was 76.7%. Substantially pure CH$_3$CF$_2$CH$_2$Cl was obtained by fractional distillation. The autoclave also contained about 77.8 grams of black residue.

Example 4B

Example 4A was repeated except that the reactants were heated to about 120° C. for about 18 hours. The crude organic layer so obtained consisted of about 58.8% CH$_3$CF$_2$CH$_2$Cl, about 28.3% CH$_3$CFClCH$_2$Cl, and about 9.8% CH$_3$CCl$_2$CH$_2$Cl. The combined yield of halopropanes was about 74%.

Example 4C

Example 4A was repeated except that no catalyst was used. The crude organic layer so obtained consisted of about 58.7% CH$_3$CF$_2$CH$_2$Cl, about 25.9% CH$_3$CFClCH$_2$Cl, and about 12.2% CH$_3$CCl$_2$CH$_2$Cl. The combined yield of halopropanes was about 80%. This example demonstrates that SbCl5 catalyst was not effective in increasing the amount of the desired CH$_3$CF$_2$CH$_2$Cl or increasing the total yield of useful products.

Example 5

Conversion of 2,3-dichloropropene to CH$_3$CFClCH$_2$Cl

A two-gallon autoclave was evacuated and charged with about 1500 grams of 2,3-dichloropropene (about 13.4 mol). It was then cooled to about −5° C. by means of internal cooling coils connected to a chiller. About 1500 grams (75 mol) was added, the chiller turned off, and the contents slowly heated to a temperature in the range of from about 20 to about 25° C. with stirring. After approximately 18 hours, the contents were cooled to about 5° C. before discharging into iced water. The organic phase was separated and washed with about 1 L of water, dried (MgSO$_4$) and filtered to give about 1554 grams of the product mixture. GC analysis indicated that the crude product contained about 86.5% CH$_3$CFClCH$_2$Cl, about 3.8% CH$_3$CF$_2$CH$_2$Cl, and about 2.8% CH$_3$CCl$_2$CH$_2$Cl. Similar results were obtained at a temperature of about 50° C., although the amount of CH$_3$CFClCH$_2$Cl decreased slightly, while the amount of CH$_3$CF$_2$CH$_2$Cl marginally increased.

Example 6

Conversion of CH$_3$CCl$_2$CH$_2$Cl to CH$_3$CF$_2$CH$_2$Cl

An autoclave was charged with about 100 grams of CH$_3$CCl$_2$CH$_2$Cl and about 44 grams of HF and the contents heated with stirring to about 130° C. for about 20.5 hours. The products were process substantially in accordance with the description in Example 1, which resulted in about 70 grams of crude product which was comprised, based on GC area %, about 43.8% CH$_3$CF$_2$CH$_2$Cl, about 23.1% CH$_3$CFClCH$_2$Cl, and about 30.3% CH$_3$CCl$_2$CH$_2$Cl. The autoclave also contained about 1.9 grams of dark residue.

Example 7

Conversion of a Mixture of CH$_3$CFClCH$_2$Cl and CH$_3$CCl$_2$CH$_2$Cl to CH$_3$CF$_2$CH$_2$Cl A mixture of about 666 grams of CH$_3$CFClCH$_2$Cl, about 268 grams of CH$_3$CCl$_2$CH$_2$Cl, about 474 grams of HF and about 11 grams of SnCl$_4$ were heated together with stirring to about 114° C. for about 18 hours. The crude product was comprised of about 89% CH$_3$CF$_2$CH$_2$Cl.

Based on the results of Examples 4-7, the use of chlorinated antimony catalyst, such as SbCl$_5$, may not be preferred in certain embodiments due to an added cost that may not provide the desired improvement in yield or conversion in some embodiments, and may produce considerable by-product residue. In certain embodiments, therefore, it is preferred to run the reaction without catalyst. However, the use of SnCl$_4$ may be preferred in embodiments in which CH$_3$CF$_2$CH$_2$Cl is the desired product, since its use may allow a lower temperature to be used and result in a higher percentage of CH$_3$CF$_2$CH$_2$Cl in the crude product.

Examples 8A-8C

Preparation of CH$_3$CF$_2$CCl$_3$

The photochlorination of CH$_3$CF$_2$CH$_3$ to CH$_3$CF$_2$CCl$_3$ has been mentioned in JACS, 59 (1937) 2436, which is incorporated herein by reference.

Example 8A

Photochlorination of CH$_3$CF$_2$CH$_2$Cl

The photochlorination was done using a 100-W Hg lamp placed in a quartz jacket that was cooled with the use of a circulating cooling bath set at about −5° C. The quartz jacket was inserted into a glass reactor of about 400 mL capacity.

The reactor was cooled externally by placing it in a glycol-water bath which was cooled with the use of cooling coils connected to a second circulating bath set at −8.5 C. The reactor was fitted with a thermocouple, stir bar, and a gas inlet tube for introducing chlorine gas from a cylinder via a calibrated flowmeter. Exiting gases passed through a water-cooled condenser, an air trap, and a scrubber containing NaOH and Na2SO3 to remove HCl and chlorine.

The reactor was charged with about 250.5 grams of $CH_3CF_2CH_2Cl$ of about 98.6% purity and allowed to cool to a substantially constant temperature of about −5.5 C. The chlorine cylinder was then opened and the flow rate set at 23 g/h. Immediately thereafter, the lamp was then turned on. After approximately 0.5 hours, the temperature of the reactor contents stabilized at about −3±0.5 C.

The photochlorination was continued for about 7 hours and a conversion of about 79.4% was achieved. The composition of the crude product, which amounted to about 309.3 grams, was about 19.2% $CH_3CF_2CH_2Cl$, about 50.9% $CH_3CF_2CHCl_2$ and about 24.8% $CH_3CF_2CCl_3$. Substantially pure $CH_3CF_2CCl_3$ was obtained by fractional distillation.

A 450-W Hg lamp could also be used. The ratios of $CH_3CF_2CHCl_2$ to $CH_3CF_2CCl_3$ vs. time were essentially the same as with a 100-watt lamp.

Example 8B

Photochlorination of $CH_3CF_2CHCl_2$

In a manner similar to that described in Example 8A, about 296.8 grams of $CH_3CF_2CHCl_2$ (about 97.4% pure, containing about 1.9% $CH_3CF_2CCl_3$) was photochlorinated using a 100-W Hg lamp at a temperature of about −4° C. and chlorine feed rate of about 22.3 g/h. After about 2.5 hours, the composition of the reactor contents was about 58.2% $CH_3CF_2CHCl_2$ and about 39.9% $CH_3CF_2CCl_3$. Thus the selectivity for $CH_3CF_2CCl_3$ was about 97% at a $CH_3CF_2CHCl_2$ conversion of about 40%.

Example 10C

Photochlorination of a Mixture of $CH_3CF_2CH_2Cl$ and $CH_3CF_2CHCl_2$

The selectivity found in Examples 8A and 8C is considered to be desirably for many embodiments of the invention. However, limiting the conversion achieved in those examples may be less than desired in certain applications. It is believed that the conversions may be limited in those example by two factors. One factor is the melting point of $CH_3CF_2CCl_3$ (53 C) and the other is lower selectivity at high conversion. The latter may be a problem in connection with certain commercial embodiments where such yield losses may be unacceptable. Therefore to keep selectivity high with relatively high conversion, it is advantageous in certain embodiments to run the photochlorination with less than 100% conversion of $CH_3CF_2CHCl_2$ and recycle this material along with fresh $CH_3CF_2CH_2Cl$, preferably in the next batch. In preferred embodiments, the amount of $CH_3CF_2CHCl_2$ made is approximately equal to the amount added as recycled material.

A mixture of about 202.4 grams of $CH_3CF_2CH_2Cl$ and about 110.7 g of $CH_3CF_2CHCl_2$ was photochlorinated using a 100-watt Hg lamp at a temperature of about −4° C. with a chlorine feed rate of about 22.2 g/h as described in Example 10A. After an irradiation time of about 8.4 hours the conversion of $CH_3CF_2CH_2Cl$ exceeded about 90%. The composition of the crude product was about 6.9 wt % $CH_3CF_2CH_2Cl$, 45.2 wt % $CH_3CF_2CHCl_2$, and 43.5 wt % $CH_3CF_2CCl_3$. The amount of $CH_3CF_2CHCl_2$ initially increased with time, reaching a maximum of about 55 wt % after about 5 hours.

Example 90A-90C

Conversion of 2,3-dichloropropene

Example 10A

About 65 cc of 50 weight % SbCl5 on activated carbon support is provided at a temperature of about 95° C. The catalyst was loaded into the ½" OD×36" L monel tube. 2,3-dichloropropene was used for the organic feed stock. After normal catalyst activation with HF and Cl2, the Cl2 flow was stopped and the HF feed was adjusted to a rate of about 47 g/hr. Shortly thereafter, the 2,3-dichloropropene feed was started at a rate of about 20-25 g/hr. The HF/organic mole ratio was 11.5/1. The pressure was about 20 psig. The contact time was about 6.73 sec. Reactor effluent samples were collected in Tedlar gas sample bags containing DI water to absorb the acid before analysis. The bags were then heated to about 60° C. to ensure that the organic present in the bag was completely vaporized. GC/MS results showed the major product to be 1-chloro-2,2-difluoropropane (262ca) with an area of about 93.3%. Also present are about 3.7 area % of 1,2,2-trifluoropropane (263ca) and about 3.4 area % of 272ca. The conversion of the 2,3-dichloropropene was about 100%.

Example 10B

This example was run similarly to Example 10A but the reaction temperature was about 135° C. The contact time was about 6.07 sec. The GC/MS results of the bag sample show about 72.8 area % for 1-chloro-2,2-difluoropropane (262ca), about 15.11 area % for 1,2-dichloro-2-fluoropropane (261ba), about 4.8 area % for 263ca, about 4.1 area % for 2,2-difluoropropane (272ca) and about 2.6 area % for 1,1,1,2,2,3,3,4,4-nanofluorohexane.

Example 10C

This Example was run similarly to Example 10A but the reaction temperature was about 195° C. The contact time was about 5.29 sec. The GC/MS results of the bag sample show about 38.59 area % for 1-chloro-2,2-difluoropropane (262ca), about 29.3 area % for 1,2-dichloro-2-fluoropropane (261ba), about 4.7 area % for 263ca, about 20.12 area % for 272ca and about 7.3 area % for 1,1,1,2,2,3,3,4,4-nanofluorohexane.

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting.

What is claimed is:
1. A method for producing fluorinated organic compounds comprising converting at least one compound of Formula (IA)

$$C(X)_3CF_2CH_3 \hspace{4em} \text{(IA)}$$

to 1,1,1,2,2-pentafluoropropane (HFC-245cb), wherein each X in Formula IA is independently H, F, Cl, I, or Br and at least one X is a chlorine wherein said converting step occurs in the presence of at least one catalyst selected from the group consisting of an Sb-based catalyst, an Fe-based catalyst, TiCl$_4$, SnCl$_4$, AlCl$_3$, AlF$_3$, and combinations thereof;

dehydrofluorinating 1,1,1,2,2-pentafluoropropane (HFC-245cb) to form 2,3,3,3-tetrafluoropropene (HFO-1234yf), wherein said dehydrofluorinating step is carried out in the absence of a catalyst or in the presence of an optionally supported catalyst selected from the group consisting of a carbon-based catalyst, a nickel-based catalyst, palladium-based catalyst, and combinations thereof.

2. The method of claim 1 wherein said at least one compound of Formula (IA) comprises at least one trichlorinated, difluorinated propane.

3. The method of claim 1 wherein said at least one compound of Formula (IA) comprises 1,1,1-trichloro-2,2-difluoropropane (HCFC-242bb).

4. The method of claim 1 wherein said converting step comprises at least one gas phase catalytic reaction.

5. The method of claim 1 further comprising the step of providing said compound of Formula (IA) by converting at least one compound of Formula (III):

to at least one compound of Formula (IA), where each X in Formula III is independently H, F, Cl, I or Br, provided at least one X is Cl, I or Br.

6. The method of claim 5 wherein at least one X on the unsaturated carbon of Formula (III) is Cl, I or Br.

7. The method of claim 5 wherein at least one X on the unsaturated carbon of Formula (III) is Cl.

8. The method of claim 5 wherein converting step comprises converting said compound of Formula (III) in the presence of a catalyst.

9. A method for producing fluorinated organic compounds comprising converting at least one compound of Formula (I)

to at least one compound of Formula (II)

where each X and Z is independently H, F, Cl, I or Br, wherein said at least one compound of Formula (I) comprises at least a first compound of Formula (IA)

wherein X is independently H, F, Cl, I or Br, wherein said first compound of Formula (IA) is not pentafluorinated, and wherein said converting step comprises a first reaction stage of converting said first compound of Formula (IA) to a second compound of Formula (IA) wherein said second compound is pentafluorinated and a second reaction stage where the second compound of Formula (IA) is converted to form at least one compound of Formula II.

10. The method of claim 9 wherein said first reaction stage comprises a gas phase catalytic reaction.

11. The method of claim 9 wherein said second compound of Formula (IA) comprises HFC-245cb.

12. The method of claim 9 wherein said first reaction stage includes at least a first catalyst and said second reaction stage includes at least a second catalyst.

13. The method of claim 9 wherein said first reaction stage comprises a fluorination reaction stage containing at least a first fluorination catalyst.

14. The method of claim 13 wherein said first fluorination catalyst comprises a Sb-based catalyst.

15. The method of claim 13 wherein said first fluorination catalyst comprises a Fe-based catalyst.

16. The method of claim 12 wherein said second catalyst comprises a metal-based catalyst.

17. The method of claim 12 wherein said second catalyst comprises a nickel-based catalyst.

18. The method of claim 12 wherein said second catalyst comprises a carbon-based catalyst.

19. The method of claim 9 wherein said compound of Formula (II) comprises HFO-1234yf.

* * * * *